US006274765B1

(12) United States Patent
Borchert et al.

(10) Patent No.: US 6,274,765 B1
(45) Date of Patent: Aug. 14, 2001

(54) PROCESS AND CATALYST FOR PREPARING ACETIC ACID BY CATALYTIC OXIDATION OF ETHANE

(75) Inventors: Holger Borchert, Bockenheim; Uwe Dingerdissen, Seeheim-Jurgenheim; Ranier Roesky, Frankfurt, all of (DE)

(73) Assignee: Hoechst Research & Technology Deutschland GmbH & Co. KG

( * ) Notice: Subject to any disclaimer, the term of this patent is extended or adjusted under 35 U.S.C. 154(b) by 0 days.

(21) Appl. No.: 09/403,516

(22) PCT Filed: Apr. 11, 1998

(86) PCT No.: PCT/EP98/02124
§ 371 Date: Nov. 10, 1999
§ 102(e) Date: Nov. 10, 1999

(87) PCT Pub. No.: WO98/47850
PCT Pub. Date: Oct. 29, 1998

(30) Foreign Application Priority Data

Apr. 23, 1997 (DE) .............................................. 197 17 076

(51) Int. Cl.$^7$ .................................................. C07C 51/215
(52) U.S. Cl. .......................... 562/549; 562/548; 562/607; 502/305
(58) Field of Search .................................. 562/548, 549, 562/607; 502/215, 305–320

(56) References Cited

U.S. PATENT DOCUMENTS 5,300,682 * 4/1994 Blum et al. .

FOREIGN PATENT DOCUMENTS

| 0407091 | 1/1991 | (EP) . |
| 0480594 | 4/1992 | (EP) . |
| 0620205 | 10/1994 | (EP) . |
| 0801799 | 10/1997 | (EP) . |

* cited by examiner

Primary Examiner—Paul J. Killos
Assistant Examiner—Robert W. Deemie
(74) Attorney, Agent, or Firm—Bierman, Muserlian and Lucas

(57) ABSTRACT

A process is disclosed for selectively preparing acetic acid from a gaseous feed of ethane, ethylene or mixtures thereof, as well as oxygen, at an increased temperature, on a catalyst which contains the elements W, X, Y and Z in the gram-atom ratio a:b:c:d, associated with oxygen. In the formula $W_aX_bY_cZ_d$ (I), X stands for one or several elements selected from the group Pd, Pt, Ag and/or Au; Y stands for one or several elements selected from the group V, Nb, Cr, Mn, Fe, Sn, Sb, Cu, Zn, U, Ni and/or Bi; Z stands for one or several elements selected from the group Li, Na, K, Rb, Cs, Be, Mg, Ca, Sr, Ba, Sc, Y, La, Ti, Zr, Hf, Ru, Os, Co, Rh, Ir, B, Al, Ga, In, Tl, Si, Ge, Pb, P, As and/or Te; a equals 1, b is a number higher than 0, c is a number higher than 0, and d is a number from 0 to 2. Also disclosed is said catalyst.

11 Claims, No Drawings

PROCESS AND CATALYST FOR PREPARING ACETIC ACID BY CATALYTIC OXIDATION OF ETHANE

The present invention relates to a process for the selective preparation of acetic acid by catalytic gas-phase oxidation of ethane and/or of ethylene in the presence of a tungsten-containing catalyst, and to the catalyst.

The oxidative dehydrogenation of ethane to ethylene in the gas phase at temperatures >500° C. is disclosed, for example in U.S. Pat. Nos. 4,250,346, 4,524,236 and 4,568,790. Thus, U.S. Pat. No. 4,250,346 discloses the use of a catalyst composition which contains the elements molybdenum, X and Y in the ratio a:b:c for converting ethane into ethylene, in which X is Cr, Mn, Nb, Ta, Ti, V and/or W, and Y is Bi, Ce, Co, Cu, Fe, K, Mg, Ni, P, Pb, Sb, Si, Sn, Tl and/or U, and a is 1, b is 0.05 to 1 and c is 0 to 2. The total value of c for Co, Ni and/or Fe must in this case be less than 0.5. The reaction is preferably carried out in the presence of added water. The disclosed catalysts may likewise be used for oxidizing ethane to acetic acid, in which case the efficiency of the conversion to acetic acid is about 18%, with an ethane conversion of 7.5%.

EP-A-0 294 845 discloses a process for the selective preparation of acetic acid from ethane, ethylene or mixtures thereof with oxygen in the presence of a catalyst mixture containing A.) a calcined catalyst of the formula $Mo_xV_y$ or $Mo_xV_yZ_y$ in which Z can be one or more of the metals Li, Na, Be, Mg, Ca, Sr, Ba, Zn, Cd, Hg, Sc, Y, La, Ce, Al, Tl, Ti, Zr, Hf, Pb, Nb, Ta, As, Sb, Bi, Cr, W, U, Te, Fe, Co and Ni, x is 0.5 to 0.9, y is 0.1 to 0.4 and z is 0.001 to 1, and B.) an ethylene hydration catalyst and/or ethylene oxidation catalyst. The second catalyst component B is, in particular, a molecular sieve catalyst or a palladium-containing oxidation catalyst. The maximum selectivity which can be achieved is 27% with an ethane conversion of 7%. The high ethane conversion rates are, according to EP-A-0 294 845, achieved only with the catalyst mixture described, but not with a single catalyst containing the components A and B.

EP-A-0 407 091 discloses a process for preparing a mixture of ethylene and/or acetic acid. In this case, ethane and/or ethylene and a gas containing molecular oxygen are brought into contact at elevated temperature with a catalyst composition which contains the elements A, X and Y. A in this case is Mo/Re/W, X is Cr, Mn, Nb, Ta, Ti, V and/or W and Y is Bi, Ce, Co, Cu, Fe, K, Mg, Ni, P, Pb, Sb, Si, Sn, Tl and/or U. The maximum selectivities which it was possible to achieve on use of the described catalyst for the oxidation of ethane to acetic acid are 78%. Other byproducts formed are carbon dioxide, carbon monoxide and ethylene.

Said publications disclose catalysts which comprise molybdenum as main component. Catalysts which comprise molydenum are, however, disadvantageous because, under the prevailing reaction conditions, molybdenum forms volatile molybdenum compounds which lead to a decrease in the activity and selectivity of the catalyst.

None of the publications listed above discloses the use of a catalyst which comprises tungsten and a noble metal for the selective oxidation of ethane and/or ethylene to acetic acid. Furthermore, the selectivities achieved for this oxidation to date in the prior art are unsatisfactory.

The object therefore was to provide a process with which ethane and/or ethylene can be oxidized in a simple manner, specifically and with high selectivity under reaction conditions which are as mild as possible to acetic acid.

It has been found, surprisingly, that it is possible on use of a catalyst which comprises tungsten in combination with a noble metal (for example Pd, Pt, Ag and Au) and one or more elements from the group of vanadium, niobium, tantalum to oxidize ethane and/or ethylene under relatively mild conditions in a simple manner with high selectivity to acetic acid. Tungsten oxide is far less volatile than molybdenum oxide. Thus, the catalysts according to the invention which comprise tungsten in place of molybdenum prove to be stable in respect of their activity and selectivity over a long period.

The present invention thus relates to a process for the selective preparation of acetic acid from a gaseous feedstock of ethane, ethylene or mixtures thereof, and oxygen or oxygen-containing gases, at elevated temperature on a tungsten-containing catalyst which comprises the elements W, X, Y and Z in the gram-atom ratios a:b:c:d in combination with oxygen $$W_aX_bY_cZ_d \quad (I)$$

in which

X is one or more elements selected from the group of Pd, Pt, Ag and/or Au,

Y is one or more elements selected from the group of V, Nb, Cr, Mn, Fe, Sn, Sb, Cu, Zn, U, Ni and/or Bi, Z is one or more elements selected from the group of Li, Na, K, Rb, Cs, Be, Mg, Ca, Sr, Ba, Sc, Y, La, Ti, Zr, Hf, Ru, Os, Co, Rh, Ir, B, Al, Ga, In, Tl, Si, Ge, Pb, P, As and/or Te, a is 1, b is a number greater than 0, c is a number greater than 0, and d is a number from 0 to 2.

X is preferably Pd, Y is preferably V, Nb, Sb and/or Cu, and Z is preferably K, Ca, Si and/or P.

Where X, Y and Z are several different elements, the indices b, c and d can likewise assume several different values.

The present invention further relates to a catalyst for the selective preparation of acetic acid comprising the elements W, X, Y and Z in the gram-atom ratios a:b:c:d in combination with oxygen.

The stoichiometric indices b, c and d are preferably:

b 0.0001 to 0.5;

c 0.1 to 1.0, and d 0.001 to 1.0.

Values of b above the preferred range may lead to a favoring of the formation of carbon dioxide in the process according to the invention. By contrast, with contents below the stated preferred range there is observed to be a preference for the formation of ethylene. The preferred values for b additionally permit the invention to be carried out particularly economically.

In another preferred embodiment, the catalyst according to the invention comprises, apart from the elements tungsten and palladium, also vanadium, niobium and/or antimony and calcium in combination with oxygen. The gram-atom ratios $a:b:c^1:c^2:c^3:d^1$ of the elements W:Pd:V:Nb:Sb:Ca are preferably as follows:

a(W)=1;

b(Pd)=0.0001 to 0.5, in particular 0.0002 to 0.05;

$c^1$(V)=0.1 to 1.0;

$c^2$(Nb)=0.1 to 0.5;

$c^3(Sb)$=0 to 0.5;
$d^1(Ca)$=0 to 0.2.

Examples of catalysts which are particularly preferably employed in the process according to the invention are:

$W_{1.00}Pd_{0.0005}V_{0.50}Nb_{0.12}$
$W_{1.00}Pd_{0.0005}V_{0.75}Nb_{0.20}$
$W_{1.00}Pd_{0.0004}V_{0.50}Nb_{0.20}Cu_{0.10}P_{0.05}$
$W_{1.00}Pd_{0.0005}V_{0.50}Nb_{0.12}Sb_{0.10}Ca_{0.02}$
$W_{1.00}Pd_{0.0004}Au_{0.0001}V_{0.75}Nb_{0.25}Te_{0.002}$
$W_{1.00}Pd_{0.0005}Ag_{0.0001}V_{0.75}Nb_{0.12}Si_{0.01}$

The catalysts according to the invention can be prepared by processes described in the prior art. These start from a suspension, in particular an aqueous solution, which comprises the individual starting components of the elements appropriate for their proportions.

The starting materials of the individual components for preparing the catalyst according to the invention are, besides the oxides, preferably water-soluble substances such as ammonium salts, nitrates, sulfates, halides, hydroxides and salts of organic acids which can be converted by heating into the corresponding oxides. To mix the components, aqueous solutions or suspensions of the metal compounds are prepared and mixed.

Advisable starting materials for tungsten are, because of the commercial availability, the corresponding tungstates such as, for example, ammonium tungstate.

The resulting reaction mixture is then stirred at 50 to 100° C. for 5 minutes to 5 hours. The water is subsequently removed, and the remaining catalyst is dried at a temperature of 50 to 150° C., in particular 80 to 120° C.

In the case where the resulting catalyst is subsequently subjected to a calcination process, it is advisable to calcine the dried and powdered catalyst at a temperature in the range from 100° C. to 800° C., in particular 200 to 500° C., in the presence of nitrogen, oxygen or an oxygen-containing gas. The duration of the calcination is preferably 2 to 24 hours.

The catalyst can be employed without an appropriate carrier material or be mixed with one such or applied to one such. Conventional carrier materials are suitable, such as, for example, porous silicon dioxide, fused silicon dioxide, kieselguhr, silica gel, porous or nonporous aluminum oxide, titanium dioxide, zirconium dioxide, thorium dioxide, lanthanum dioxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride or silicon carbide, but also glass fibers, carbon fibers, metal oxide meshes or metal meshes, or corresponding monoliths.

If the catalyst is applied to a carrier, this can take place by dry or wet impregnation of the carrier with the dissolved or suspended components of the catalyst. Another possibility is for solutions or suspensions of the catalyst components to be mixed with a sol of the carrier material and subsequently subjected to a spray drying. In both cases, calcination can be carried out subsequently as described.

Preferred carrier materials have a surface area of less than 100 m²/g. Preferred carrier materials are silicon dioxide and aluminum oxide with a low specific surface area. The catalyst can be employed after shaping as regularly or irregularly shaped supported body, in powdered form or in the abovementioned forms as heterogeneous oxidation catalyst.

The reaction can be carried out in a fluidized bed or in a fixed bed reactor. For use in a fluidized bed, the catalyst is normally ground to a particle size in the range from 10 to 200 μm or prepared by spray drying.

The gaseous feedstock contains ethane and/or ethylene which are fed to the reactor as pure gases or in a mixture with one or more other gases. Suitable examples of such additional or carrier gases are nitrogen, methane, carbon monoxide, carbon dioxide, air and/or steam. The gas containing molecular oxygen may be air or a gas which has a higher or lower molecular oxygen concentration than air, for example pure oxygen. The proportion of steam can be in the range from 0 to 50% by volume. Higher steam concentrations would make the workup of the resulting aqueous acetic acid unnecessarily costly for technical reasons, but are technically possible. The molar ratio of ethane/ethylene to oxygen is preferably in the range between 1:1 and 10:1, in particular 2:1 and 8:1. Higher oxygen contents are preferred because the ethane conversion which can be achieved, and thus the acetic acid yield, is higher. It is preferred to add oxygen or the gas containing molecular oxygen in a concentration range outside the explosion limits under the reaction conditions, because this simplifies the carrying out of the process. However, it is also possible to adjust the ethane/ethylene/oxygen mixture within the explosion limits.

The reaction is generally carried out at temperatures between 200 and 500° C., preferably 200 to 400° C. The pressure can be atmospheric or superatmospheric, for example in the range between 1 and 50 bar, preferably 1 to 30 bar.

The reaction can be carried out in a fixed bed or fluidized bed reactor. Ethane is expediently first mixed with the inert gases such as nitrogen or steam before oxygen or the gas containing molecular oxygen is fed in. The mixed gases are preferably preheated to the reaction temperature in a preheating zone, before the gas mixture is brought into contact with the catalyst. Acetic acid is removed from the gas leaving the reactor by condensation. The other gases are returned to the reactor inlet, where oxygen or the gas containing molecular oxygen, and ethane and/or ethylene is metered in.

EXAMPLES

The catalyst composition mentioned in the examples is indicated in relative atomic ratios.

Catalyst Preparation

Catalyst (I):

A catalyst with the following composition was prepared:
$W_{1.00}Pd_{0.0005}V_{0.25}Nb_{0.12}$ 100 g of ammonium metatungstate are suspended in 500 ml of water at 90° C. A solution of 11.2 g of ammonium metavanadate in 250 ml of water at 90° C. is added dropwise to this mixture. The combined mixtures are stirred at 90° C. for 15 minutes. Then a solution of 35.7 g of niobium oxalate in 400 ml of water at 90° C. is added dropwise to this mixture. The combined solutions are stirred at 90° C. for 15 minutes. Finally, a solution of 0.043 g of palladium acetate in 50 ml of acetone is added to the resulting mixture, and the mixture is stirred at 90° C. for 15 minutes. The water is then evaporated off, and the evaporated residue is dried at 120° C. overnight. The solid is crushed (screen fraction <2 mm) and then heated under a stream of air to 400° C. at a heating rate of 2° C. per minute. The temperature is maintained for 4 hours. The stream of air is switched off, and the material is slowly cooled. The catalyst is ground and compressed (pressure 2 tons) and screened in order to obtain a screen fraction between 0.35 and 0.7 mm.

Catalyst (II):

$W_{1.00}Pd_{0.0005}V_{0.50}Nb_{0.12}$ 100 g of ammonium metatungstate are suspended in 500 ml of water at 90° C. A solution of 22.4 g of ammonium metavanadate in 250 ml of water at 90° C. is added dropwise to this mixture. The combined mixtures are stirred at 90° C. for 15 minutes. Then a solution of 35.7 g of niobium oxalate in 400 ml of water at 90° C. is added dropwise to this mixture. The combined solutions are stirred at 90° C. for 15 minutes. Finally, a solution of 0.043 g of palladium acetate in 50 ml of acetone is added to the resulting mixture, and the mixture is stirred at 90° C. for 15 minutes. The water is then evaporated off, and the evaporated residue is dried at 120° C. overnight. The solid is crushed (screen fraction <2 mm) and then heated under a stream of air to 400° C. at a heating rate of 2° C. per minute. The temperature is maintained for 4 hours. The stream of air is switched off, and the material is slowly cooled. The catalyst is ground and compressed (pressure 2 tons) and screened in order to obtain a screen fraction between 0.35 and 0.7 mm.

Catalyst (III):

$W_{1.00}Pd_{0.0005}V_{1.00}Nb_{0.12}$ 100 g of ammonium metatungstate are suspended in 500 ml of water at 90° C. A solution of 44.4 g of ammonium metavanadate in 250 ml of water at 90° C. is added dropwise to this mixture. The combined mixtures are stirred at 90° C. for 15 minutes. Then a solution of 35.7 g of niobium oxalate in 400 ml of water at 90° C. is added dropwise to this mixture. The combined solutions are stirred at 90° C. for 15 minutes. Finally, a solution of 0.043 g of palladium acetate in 50 ml of acetone is added to the resulting mixture, and the mixture is stirred at 90° C. for 15 minutes. The water is then evaporated off, and the evaporated residue is dried at 120° C. overnight. The solid is crushed (screen fraction <2 mm) and then heated under a stream of air to 400° C. at a heating rate of 2° C. per minute. The temperature is maintained for 4 hours. The stream of air is switched off, and the material is slowly cooled. The catalyst is ground and compressed (pressure 2 tons) and screened in order to obtain a screen fraction between 0.35 and 0.7 mm.

Catalyst (IV):

$W_{1.00}Pd_{0.0005}V_{0.50}Nb_{0.12}Sb_{0.10}Ca_{0.02}$ 100 g of ammonium metatungstate are suspended in 500 ml of water at 90° C. A solution of 22.4 g of ammonium metavanadate in 250 ml of water at 90° C. is added dropwise to this mixture. The combined mixtures are stirred at 90° C. for 15 minutes. Then a solution of 35.7 g of niobium oxalate, 9.7 g of antimony oxalate and 1.8 g of calcium nitrate in 400 ml of water at 90° C. is added dropwise to this mixture. The combined solutions are stirred at 90° C. for 15 minutes. Finally, a solution of 0.043 g of palladium acetate in 50 ml of acetone is added to the resulting mixture, and the mixture is stirred at 90° C. for 15 minutes. The water is then evaporated off, and the evaporated residue is dried at 120° C. overnight. The solid is crushed (screen fraction <2 mm) and then heated under a stream of air to 400° C. at a heating rate of 2° C. per minute. The temperature is maintained for 4 hours. The stream of air is switched off, and the material is slowly cooled. The catalyst is ground and compressed (pressure 2 tons) and screened in order to obtain a screen fraction between 0.35 and 0.7 mm.

Catalyst (V):

$W_{1.00}Pd_{0.0005}Ag_{0.0001}V_{0.75}Nb_{0.12}Si_{0.01}$ 100 g of ammonium metatungstate are suspended in 500 ml of water at 90° C. A solution of 33.6 g of ammonium metavanadate in 250 ml of water at 90° C. is added dropwise to this mixture. The combined mixtures are stirred at 90° C. for 15 minutes. Then a suspension of 35.7 g of niobium oxalate, 0.01 g of silver nitrate and 0.23 g of kieselguhr in 400 ml of water at 90° C. is added dropwise to this mixture. The combined solutions are stirred at 90° C. for 15 minutes. Finally, a solution of 0.043 g of palladium acetate in 50 ml of acetone is added to the resulting mixture, and the mixture is stirred at 90° C. for 15 minutes. The water is then evaporated off, and the evaporated residue is dried at 120° C. overnight. The solid is crushed (screen fraction <2 mm) and then heated under a stream of air to 400° C. at a heating rate of 2° C. per minute. The temperature is maintained for 4 hours. The stream of air is switched off, and the material is slowly cooled. The catalyst is ground and compressed (pressure 2 tons) and screened in order to obtain a screen fraction between 0.35 and 0.7 mm.

Catalyst (VI):

$W_{1.00}Pd_{0.0004}V_{0.50}Nb_{0.2}Cu_{0.10}P_{0.05}$ 100 g of ammonium metatungstate are suspended in 500 ml of water at 90° C. A solution of 22.4 g of ammonium metavanadate in 250 ml of water at 90° C. is added dropwise to this mixture. The combined mixtures are stirred at 90° C. for 15 minutes. Then a suspension of 59.5 g of niobium oxalate, 8.91 g of copper nitrate and 1.6 g of phosphoric acid (85%) in 400 ml of water at 90° C. is added dropwise to this mixture. The combined solutions are stirred at 90° C. for 15 minutes. Finally, a solution of 0.034 g of palladium acetate in 50 ml of acetone is added to the resulting mixture, and the mixture is stirred at 90° C. for 15 minutes. The water is then evaporated off, and the evaporated residue is dried at 120° C. overnight. The solid is crushed (screen fraction <2 mm) and then heated under a stream of air to 400° C. at a heating rate of 2° C. per minute. The temperature is maintained for 4 hours. The stream of air is switched off, and the material is slowly cooled. The catalyst is ground and compressed (pressure 2 tons) and screened in order to obtain a screen fraction between 0.35 and 0.7 mm.

Catalyst (VII):

$W_{1.00}Pd_{0.0003}Au_{0.0001}V_{0.75}Nb_{0.25}Te_{0.002}$ 100 g of ammonium metatungstate are suspended in 500 ml of water at 90° C. A solution of 22.4 g of ammonium metavanadate in 250 ml of water at 90° C. is added dropwise to this mixture. The combined mixtures are stirred at 90° C. for 15 minutes. Then a solution of 74.4 g of niobium oxalate, 0.015 g of tetrachloroauric acid and 0.18 g of telluric acid in 400 ml of water at 90° C. is added dropwise to this mixture. The combined solutions are stirred at 90° C. for 15 minutes. Finally, a solution of 0.026 g of palladium acetate in 50 ml of acetone is added to the resulting mixture, and the mixture is stirred at 90° C. for 15 minutes. The water is then evaporated off, and the evaporated residue is dried at 120° C. overnight. The solid is crushed (screen fraction <2 mm) and then heated under a stream of air to 400° C. at a heating rate of 2° C. per minute. The temperature is maintained for 4 hours. The stream of air is switched off, and the material is slowly cooled. The catalyst is ground and compressed (pressure 2 tons) and screened in order to obtain a screen fraction between 0.35 and 0.7 mm.

Method for Testing Catalysts 10 ml of the catalyst were loaded into a steel reactor with an internal diameter of 10 mm. The catalyst was heated to 250° C. under a stream of air. The pressure was then adjusted by means of an admission pressure controller. The required ethane/oxygen/nitrogen mixture was metered with water into a vaporizing zone where water was vaporized and mixed with the gases. The reaction temperature was measured with a thermal element in the catalyst bed. The reaction gas was analyzed by on-line gas chromatography.

The following terms in the examples are defined as:

ethane conversion (%)=100×([CO]/2+[CO$_2$]/2+[C$_2$H$_4$]+ [CH$_3$COOH])/([CO]/$_2$+[CO$_2$]/2+[C$_2$H$_4$]+[C$_2$H$_6$]+[CH$_3$COOH])

ethylene selectivity (%)=100×([C$_2$H$_4$])/([CO]/$_2$+[CO$_2$]/2+[C$_2$H$_4$]+ [CH$_3$COOH])

Acetic acid selectivity (%)=100×([CH$_3$COOH])/([CO]/$_2$+[CO$_2$]/2+ [C$_2$H$_4$]+[CH$_3$COOH])

in which

[ ]=concentrations in mol % and

[$C_2H_6$]=concentration of unreacted ethane.

The holdup time is defined as:

t(s)=bulk volume of the catalyst (ml)/volumetric flow of the gas through the reactor based on the reaction conditions (ml/s)

Reaction Procedure

The reactor feed gas consisted of 40% by volume ethane, 8% by volume oxygen, 32% by volume nitrogen and 20% by volume steam. The reaction conditions and results are summarized in the following table.

| Ex. | Catalyst | Temperature (° C.) | Pressure (bar) | Holdup time (s) | Ethane conversion (%) | Acetic acid selectivity (%) | Ethylene selectivity (%) | Co + $CO_2$ selectivity (%) |
|---|---|---|---|---|---|---|---|---|
| 1 | I | 280 | 15 | 30 | 7 | 57 | 2 | 41 |
| 2 | I | 290 | 15 | 30 | 8 | 56 | 3 | 41 |
| 3 | I | 300 | 15 | 30 | 9 | 56 | 3 | 41 |
| 4 | II | 260 | 15 | 30 | 8 | 76 | 1 | 23 |
| 5 | II | 280 | 15 | 30 | 10 | 74 | 2 | 24 |
| 6 | II | 280 | 30 | 15 | 10 | 75 | 3 | 22 |
| 7 | III | 260 | 15 | 30 | 9 | 81 | 0 | 19 |
| 8 | III | 270 | 15 | 30 | 11 | 79 | 0 | 21 |
| 9 | III | 280 | 15 | 30 | 11 | 78 | 1 | 21 |
| 10 | IV | 260 | 15 | 30 | 7 | 80 | 1 | 19 |
| 11 | IV | 280 | 15 | 30 | 10 | 75 | 4 | 21 |
| 12 | V | 250 | 15 | 25 | 8 | 78 | 1 | 21 |
| 13 | V | 260 | 15 | 20 | 9 | 77 | 3 | 20 |
| 14 | VI | 250 | 15 | 20 | 10 | 80 | 1 | 19 |
| 15 | VII | 280 | 15 | 30 | 8 | 77 | 2 | 21 |

What is claimed is:

1. A process for the selective preparation of acetic acid from a gaseous feedstock of ethane, ethylene or mixtures thereof, and oxygen or oxygen-containing gases, at elevated temperature on a tungsten-containing catalyst which comprises the elements W, X, Y and Z in the gram-atom ratios a:b:c:d in combination with oxygen $$W_aX_bY_cZ_d \quad\quad\quad I$$

in which

X is at least one element selected from the group consisting of Pd, Pt, Ag and Au, Y is a plurality of elements selected from the group consisting of V, Nb, Cr, Mn, Fe, Sn, Sb, Cu, Zn, U, Ni and Bi, Z is at least one element selected from the group consisting of Li, Na, K, Rb, Cs, Be, Mg, Ca, Sr, Ba, Sc, Y, La, Ti, Zr, Hf, Ru, Os, Co, Rh, Ir, B, Al, Ga, In, Ti, Si, Ge, Pb, P, As and Te, a is 1, b is a number from 0.0001 to 0.5, c is a number from 0.1 to 1.0, and d is a number from 0 to 2, with the proviso that the catalyst contains, as Y, at least the elements V and Nb.

2. The process as claimed in claim 1, wherein X, Y and/or Z are each several elements, where the indices b, c and d can assume different values for different elements.

3. The process as claimed in claim 1 and/or 2, wherein the reaction temperature is 200 to 500° C., preferably 200 to 400° C.

4. The process as claimed in claim 1, wherein the pressure in the reactor is between 1 and 50 bar, preferably between 1 and 30 bar.

5. The process as claimed in claim 1, wherein d is a number from 0 to 1.0.

6. The process as claimed in claim 1, wherein ethane mixed with at least one other gas is fed into the reactor.

7. The process as claimed in claim 6, wherein the other gas fed in is nitrogen, oxygen, methane, carbon monoxide, carbon dioxide, ethylene and/or steam.

8. The process as claimed in claim 1, wherein the catalyst comprises at least one of the following compositions in combination with oxygen:

$W_{1.00}Pd_{0.0005}V_{0.05}Nb_{0.12}$ $W_{1.00}Pd_{0.0005}V_{0.75}Nb_{0.20}$ $W_{1.00}Pd_{0.0004}V_{0.50}Nb_{0.20}Cu_{0.10}P_{0.05}$ $W_{1.00}Pd_{0.0005}V_{0.50}Nb_{0.12}Sb_{0.10}Ca_{0.02}$ $W_{1.00}Pd_{0.0004}Au_{0.0001}V_{0.75}Nb_{0.25}Te_{0.002}$ $W_{1.00}Pd_{0.0005}Ag_{0.0001}V_{0.75}Nb_{0.12}Si_{0.01}$.

9. The process as claimed in claim 1, wherein the catalyst is mixed with a carrier material or is immobilized on a carrier material.

10. The process as claimed in claim 1, wherein the molar ratio of ethane/ethylene to oxygen is between 1:1 and 10:1, preferably between 2:1 and 8:1.

11. A tungsten-containing catalyst for the selective preparation of acetic acid from ethane, ethylene or mixtures thereof, and oxygen, comprising the elements W, X, Y and Z in the gram-atom ratios a:b:c:d in combination with oxygen $$W_aX_bY_cZ_d \quad\quad\quad I$$

in which

X is at least one element selected from the group consisting of Pd, Pt, Ag and Au, Y is a plurality of elements selected from the group consisting of V, Nb, Cr, Mn, Fe, Sn, Sb, Cu, Zn, U, Ni and Bi, Z is at least one element selected from the group consisting of Li, Na, K, Rb, Cs, Be, Mg, Ca, Sr, Ba, Sc, Y, La, Ti, Zr, Hf, Ru, Os, Co, Rh, Ir, B, Al, Ga, In, Ti, Si, Ge, Pb, P ad As and Te, a is 1, b is a number from 0.0001 to 0.5, c is a number from 0.1 to 1.0, and d is a number from 0 to 2, with the proviso that the catalyst contains, as Y, at least the elements V and Nb.

* * * * *